United States Patent [19]

Grant

[11] Patent Number: 5,641,895

[45] Date of Patent: Jun. 24, 1997

[54] DYNAMIC CONTAMINANT EXTRACTION MEASUREMENT FOR CHEMICAL DISTRIBUTION SYSTEMS

[75] Inventor: Donald C. Grant, Excelsior, Minn.

[73] Assignee: FSI International, Inc., Chaska, Minn.

[21] Appl. No.: 431,729

[22] Filed: May 1, 1995

[51] Int. Cl.⁶ .............................. G01N 11/00; G01N 1/00; H01F 27/10; B01D 21/26
[52] U.S. Cl. .................. 73/64.56; 73/61.41; 422/101; 137/110; 137/340; 137/625.28; 137/559; 210/607; 210/765; 210/805
[58] Field of Search ........................ 73/64.56, 61.42, 73/61.41; 422/101; 137/110, 89, 340, 625.28, 599, 101, 559; 210/765, 805, 607, 629

[56] References Cited

U.S. PATENT DOCUMENTS

| | | | |
|---|---|---|---|
| 3,469,438 | 9/1969 | Gaumer | 73/53 |
| 3,851,520 | 12/1974 | Schluter et al. | 73/23 |
| 4,082,948 | 4/1978 | Barton et al. | 250/304 |
| 4,437,082 | 3/1984 | Walsh et al. | 336/58 |
| 4,720,998 | 1/1988 | Hogue | 73/444 |
| 4,763,514 | 8/1988 | Naito et al. | 73/19 |
| 4,878,382 | 11/1989 | Jones et al. | 73/153 |
| 5,131,266 | 7/1992 | Hassett | 73/61.41 R |
| 5,257,528 | 11/1993 | Degouy et al. | 73/53.01 |
| 5,422,019 | 6/1995 | Carman | 210/787 |
| 5,450,744 | 9/1995 | Martyn | 73/61.71 |
| 5,496,469 | 3/1996 | Scraggs et al. | 210/177 |

OTHER PUBLICATIONS

FSI Technical Report (TR 391), "Issues Involved in Qualifying Chemical Delivery Systems for Metallic Extractables," Jun. 4, 1993, 11 pages.
FSI International, ChemFill Model 1000 Chemical Management Systems Product Data Sheet, 1993, 2 pages.

*Primary Examiner*—Hezron E. Williams
*Assistant Examiner*—J. David Wiggins
*Attorney, Agent, or Firm*—Faegre & Benson

[57] ABSTRACT

A method for qualifying a chemical distribution system and components used therein to ensure that the quantity of contaminants extracted from the system by the chemical is below a predetermined specification level. A volume of the chemical is continuously circulated through the system. The concentrations of extracted contaminants in the chemical are periodically measured, and the contaminant extraction rate determined as a function of the measurements. The system is qualified for production when the extraction rate has decreased to the specification level.

12 Claims, 4 Drawing Sheets

DYNAMIC CONTAMINANT EXTRACTION MEASUREMENT FOR CHEMICAL DISTRIBUTION SYSTEMS

BACKGROUND OF THE INVENTION

1. Field of the Invention

The present invention is a method for measuring the amount of inorganic metals and other contaminants that are extracted from a component upon exposure to liquids. In particular, the present invention is a method for dynamically measuring the extraction of contaminants from components of a chemical distribution system.

2. Description of the Related Art

Chemical distribution systems are commonly used to provide process chemicals from a central location to points of use in semiconductor fabrication facilities. Systems of this type are commercially available from a number of suppliers including FSI International of Chaska, Minn. Since the manufacturing yield and performance of semiconductor devices are sensitive to inorganic and other contaminants such as aluminum, calcium, iron and sodium, high-purity chemicals are used in the fabrication process.

Chemical distribution systems contain many components such as tanks, valves, filters and tubing that have the potential to add contaminants to the chemical being distributed. These contaminants are present both on the component surfaces exposed to the chemical, and in the bulk of the components. Following their assembly and installation at the semiconductor fabrication facility, and before being used in production, chemical distribution systems are therefore qualified to ensure that the concentrations of contaminants being added to the chemical by the system are below acceptable specification levels.

Qualification of chemical distribution systems requires the removal of the surface and bulk contaminants. Although the surface contaminants can be relatively easily removed by rinsing, the bulk contaminants must be removed by extraction. Conventional procedures for extracting contaminants are disclosed generally in the Grant et al. article, Issues Involved in *Qualifying Chemical Delivery Systems for Metallic Extractables*, published in FSI Technical Report TR 391 (June, 1993). In general, the extraction procedure disclosed in the Grant et al. article involves filling the system with chemical and allowing the chemical to remain in the system for a fixed period of time. Extraction is monitored by taking simultaneous samples of the chemical entering the system and at various locations throughout the system. The samples are then analyzed for contaminant concentrations. The change in concentration between the various sample points is assumed to be caused by extraction from the delivery system. If the change in concentration exceeds the specification, the chemical is drained from the system and the process repeated.

The decreasing feature size and continuing increase in the complexity of semiconductor devices makes the devices increasingly sensitive to contamination. Unfortunately, the conventional qualification procedures described above have a number of drawbacks. They are, for example, subject to a relatively large potential for error. Sources of error include sample collection and handling, and variations in the background contaminant levels of the incoming chemical. The procedures are also relatively inefficient since continuing supplies of incoming chemical are required. They also provide information on the extraction characteristics of the systems only over the extraction period that the samples are taken.

There is, therefore, a continuing need for improved chemical extraction and qualification procedures. In particular, there is a need for faster and more accurate and efficient extraction and qualification procedures. Procedures of this type that can also be used to accurately predict the future extraction characteristics of the system would be especially desirable.

SUMMARY OF THE INVENTION

The present invention is a dynamic method for quickly, efficiently and accurately measuring the extraction of contaminants from one or more components upon exposure to a liquid chemical. The method includes continuously circulating a volume of the chemical past the component. Concentrations of the extracted contaminants in the volume of chemical are periodically measured. In one embodiment, a known volume of the chemical is circulated past the components. The mass of the extracted contaminants can then be determined from the measured concentrations.

The invention can be used to qualify a chemical distribution system to ensure that the quantity of contaminants extracted from the system by the chemical is below a predetermined specification level. A volume of the chemical is continuously circulated through the system. The concentration of extracted contaminants in the chemical are periodically measured, and the contaminant extraction rate determined as a function of time based on the measurements. The system is qualified for production when the extraction rate has decreased to the specification level.

DETAILED DESCRIPTION OF THE PREFERRED EMBODIMENTS

The present invention is a method for dynamically measuring the extraction of inorganic and other contaminants from one or more components exposed to liquid chemical. As described in greater detail below, a volume of the liquid chemical is continuously circulated by the components to be tested, and the concentration of contaminants in the chemical periodically measured. If the volume of the circulating chemical is known, the mass of the extracted contaminants can be determined. The rate of contaminant extraction can also be determined. The method offers considerable advantages over known contaminant extraction measurement techniques, and is particularly useful for qualifying chemical distribution systems such as those used in semiconductor fabrication facilities.

Figure 1:
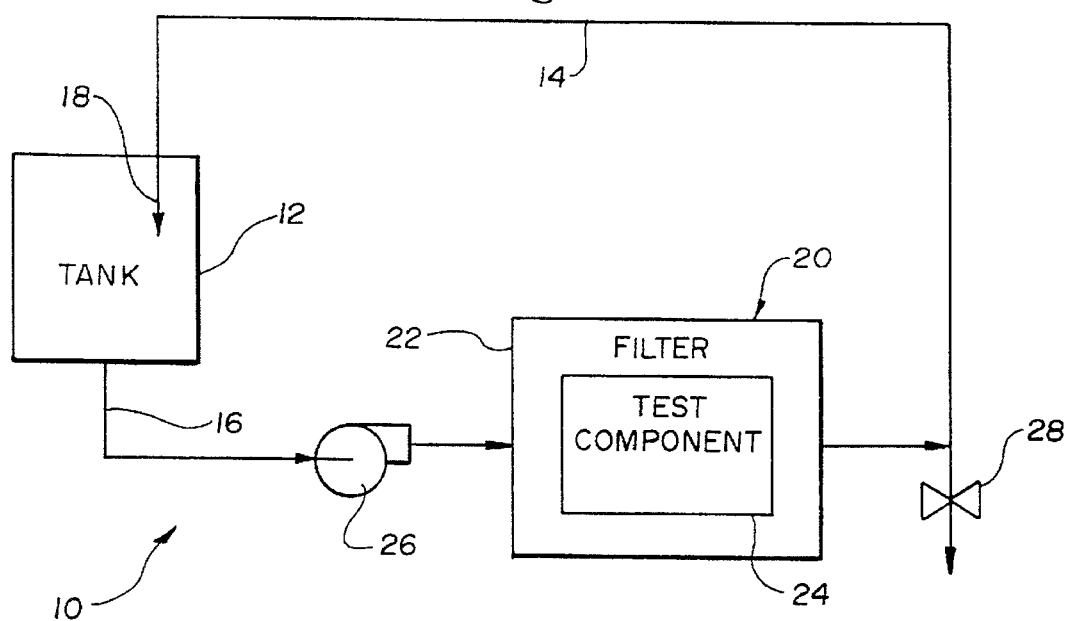
FIG. 1 is a block and diagrammatic illustration of a chemical handling system used to perform and test the dynamic contaminant extraction measurement method of the present invention.

FIG. 1 is an illustration of a system 10 used to test the dynamic extraction measurement method. As shown, system 10 includes a tank 12 and a fluid circulation tube or line 14 having both an inlet 16 and outlet 18 in the tank. A 0.05 µm microporous membrane filter 20, which is commercially available from Parker Hannifin Corp. of Lebanon, Ind., is fluidly connected in the circulation line 14. The filter 20 includes a housing 22 which forms a chamber in which filter cartridges 24 are removably mounted. Liquid chemical from tank 12 is continuously circulated through line 14 and filter 20 by pump 26. Samples of the circulated chemical are removed from circulation line 14 through sample valve 28. All portions of tank 12, line 14, pump 26 and filter housing 22 that are exposed to the chemical are "TEFLON" polytetrafluoroethylene (PTFE) or perfluoroalkoxy (PFA).

System 10 was used to evaluate the extraction of metallic elements from filter cartridges 24 (i.e., the tested components) by a chemical comprising 49% hydrofluoric acid (HF) in deionized (DI) water. Gigabit grade 49% HF from Ashland Chemical was used in the tests. This chemical contains less than one part per billion (ppb) of most contaminants. Several tests were performed using a number of different types of filter cartridges. All of the tested cartridges were ten inch long, all-PTFE units with perfluoroelastomer 0-rings. The extracted quantities of thirty-four elements, including eleven key elements (aluminum, barium, calcium, chromium, copper, iron, magnesium, potassium, sodium, titanium and zinc) were measured in each sample. Samples were collected in PFA bottles which were precleaned to minimize metallic extractables. The quantities of contaminants in the samples were measured using a combination of inductively coupled plasma-mass spectroscopy (ICP-MS) and graphite furnace atomic absorption (GFAA).

Before use in the tests described herein, system 10 was cleaned by circulating 49% HF for about two weeks. To ensure that there was minimal contaminant extraction from the components of system 10 other than the filter cartridges 24, the test procedure described below was first performed with no cartridge in the housing 22. This test confirmed that the background extraction level was minimal.

All the components were tested in system 10 using the following procedure. After the filter cartridges 24 were mounted in the housing 22, the housing was filled with high purity isopropyl alcohol (IPA) using pump 26. The IPA was maintained in the filter 20 for five minutes to ensure that the cartridges 24 were fully wetted. After the wetting period the filter 20 was flushed with high purity DI water to remove the IPA from the system, and the bulk of the water removed from the system. Tank 12 was then filled with the 49% HF chemical, and pump 26 actuated to initiate circulation of the chemical through line 14. To maximize test sensitivity, the volume of chemical in the system 10 is kept to a minimum by filling tank 12 with a volume equal to the system holdup volume plus enough chemical for sampling. A sample of the chemical used to fill tank 12 was also retained to measure the background or starting contaminant concentrations.

Samples of the circulating chemical were periodically removed from line 14 through valve 28. During the tests described herein the samples were taken at generally evenly spaced intervals on a logarithmic time scale to maximize the accuracy of the subsequent data analysis. The first sample was taken 0.1 hours after the chemical circulation was initiated. The chemical was circulated for a minimum test period of about two weeks, but typically for four to six weeks.

Figure 2:
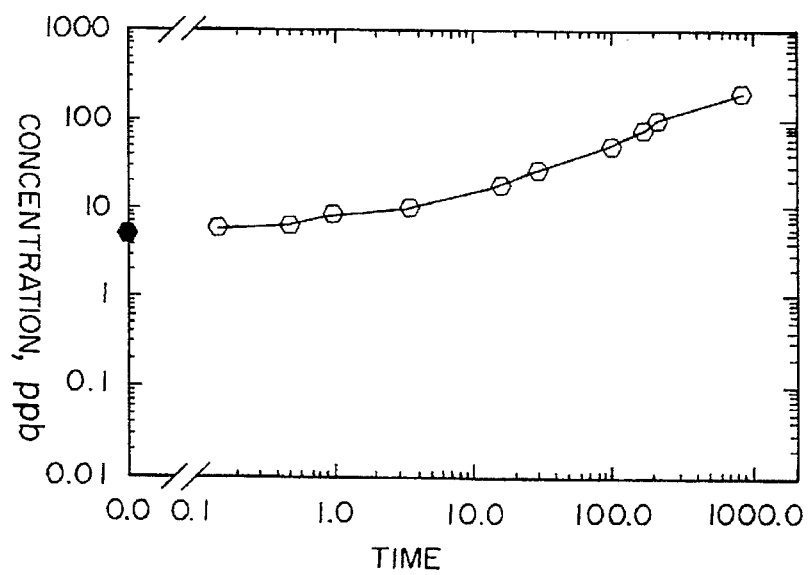
FIG. 2 is a graph of measured extracted contaminant concentration from a test component as a function of extraction time, obtained by performing the method of the present invention on the test component in the chemical handling system shown in FIG. 1.

FIG. 2 is a graph of the total extracted concentration (in parts per billion (ppb) or µg/liter) of the measured contaminants as a function of extraction time from one of the tests. The graph shown in FIG. 2 is based on ten samples taken over an extraction test period of about nine hundred hours. The background concentration is shown at time zero in FIG. 2.

Figure 3:
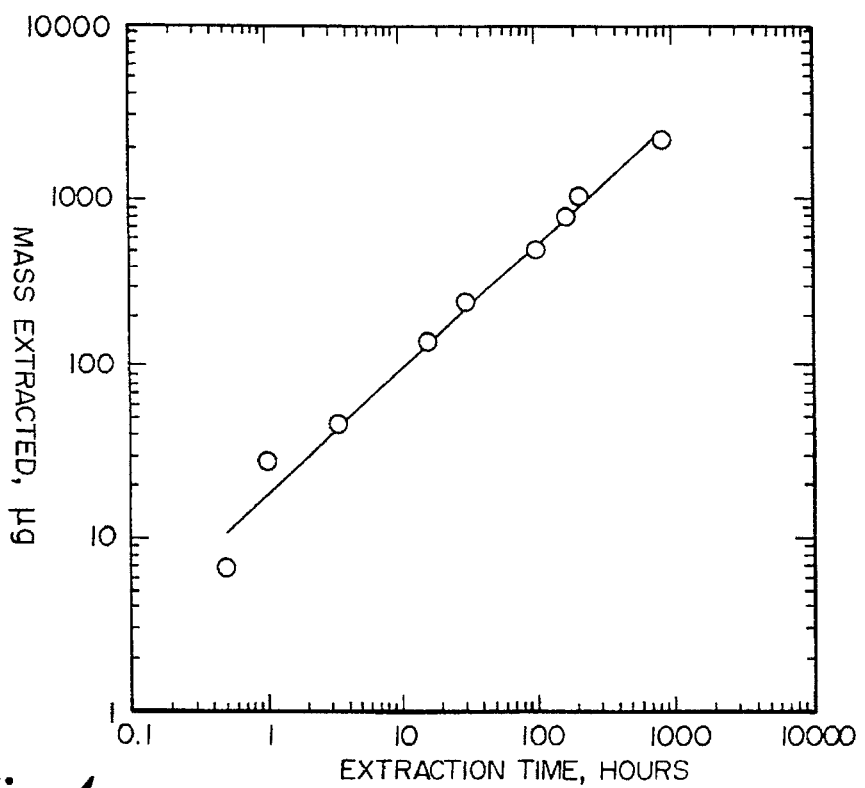
FIG. 3 is a graph of measured contaminant mass extracted from the test component as a function of extraction time, obtained from the test data shown in FIG. 2.

FIG. 3 is a graph of the total measured extracted mass as a function of extraction sample time, and is based on the concentration measurements shown in FIG. 2. The difference between the measured contaminant concentration in the 0.1 hour sample and the background concentration is presumed to be the amount of surface contaminants from the cartridge, while concentration increases in samples taken after 0.1 hours are presumed to be due to extraction from the bulk material. Using this assumption and the measured contaminant concentrations, the total extracted contaminant mass at each of the 0.5 hour and subsequent sample times can be computed by subtracting the 0.1 hour sample concentration from the measured contaminant concentration at each of the sample times, and multiplying by the volume of circulating chemical in the system 10. The reduction in circulating chemical volume due to sample removal was taken into account when calculating the total mass of extracted contaminants. The line shown in FIG. 3 represents a least squares best fit to the data points, and is described by Equation 1 below.

$$M_T = 18 t^{0.739} \qquad \text{Eq. 1}$$

Where:

t=time in hours; and $M_T$=mass in micrograms.

The slope of the line is very close to the 0.5 value predicted by theory. Deviations from theory may be due to the geometry of the cartridge 24 (the theory value was based on an infinite plane of uniform thickness) and nonuniform distribution of contaminants in the cartridge.

Figure 4:
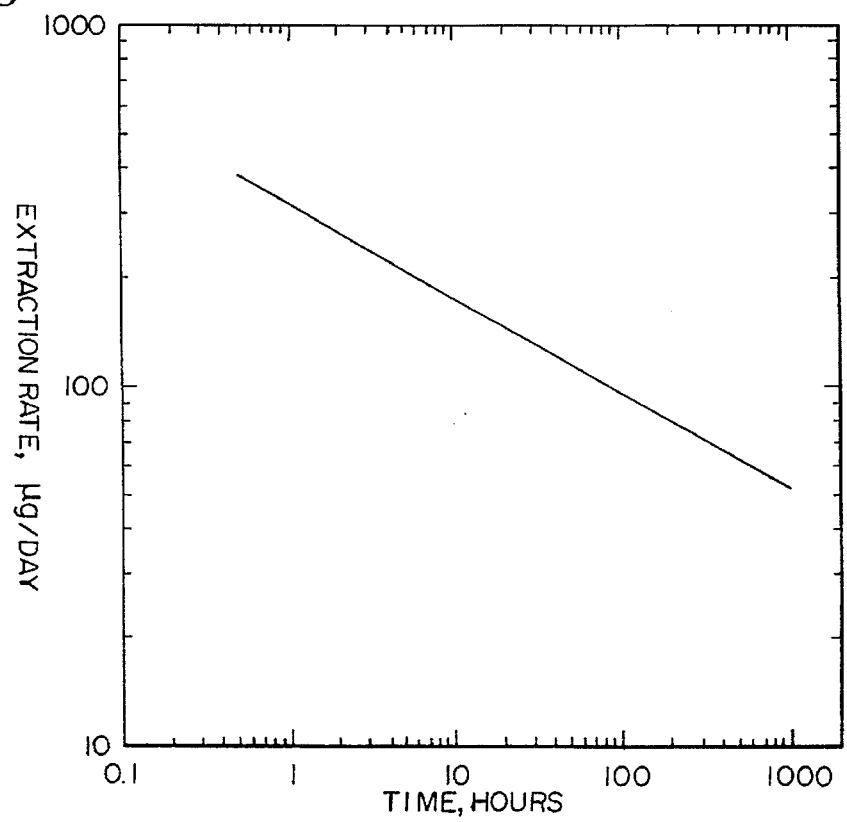
FIG. 4 is a graph of measured contaminant concentration extraction rate as a function of extraction time, obtained from the test data shown in FIG. 3.

FIG. 4 is a graph of the extraction rate as a function of extraction time. The data forming the graph in FIG. 4 was obtained by taking the derivative of the line shown in FIG. 3. When derived from Equation 1, the extraction rate is described by Equation 2 below.

$$R_T = 319 t^{-0.261} \qquad \text{Eq. 2}$$

Where:

t=time in hours; and $R_T$=extraction rate in micrograms/day.

Equation 2 can be used to predict the amount of contamination that will be added to the chemical by filter cartridges 24 if the filters are installed in a chemical delivery system. For example, Equation 3 below which describes the amount of contamination added to a system processing two hundred liters of chemical per day is derived by dividing Equation 2 by two hundred.

$$C_A = 1.60 \, t^{-0.261} \qquad \text{Eq. 3}$$

Where:

t=time in hours; and $C_A$=micrograms/liter (equivalent to ppb).

Figure 5:
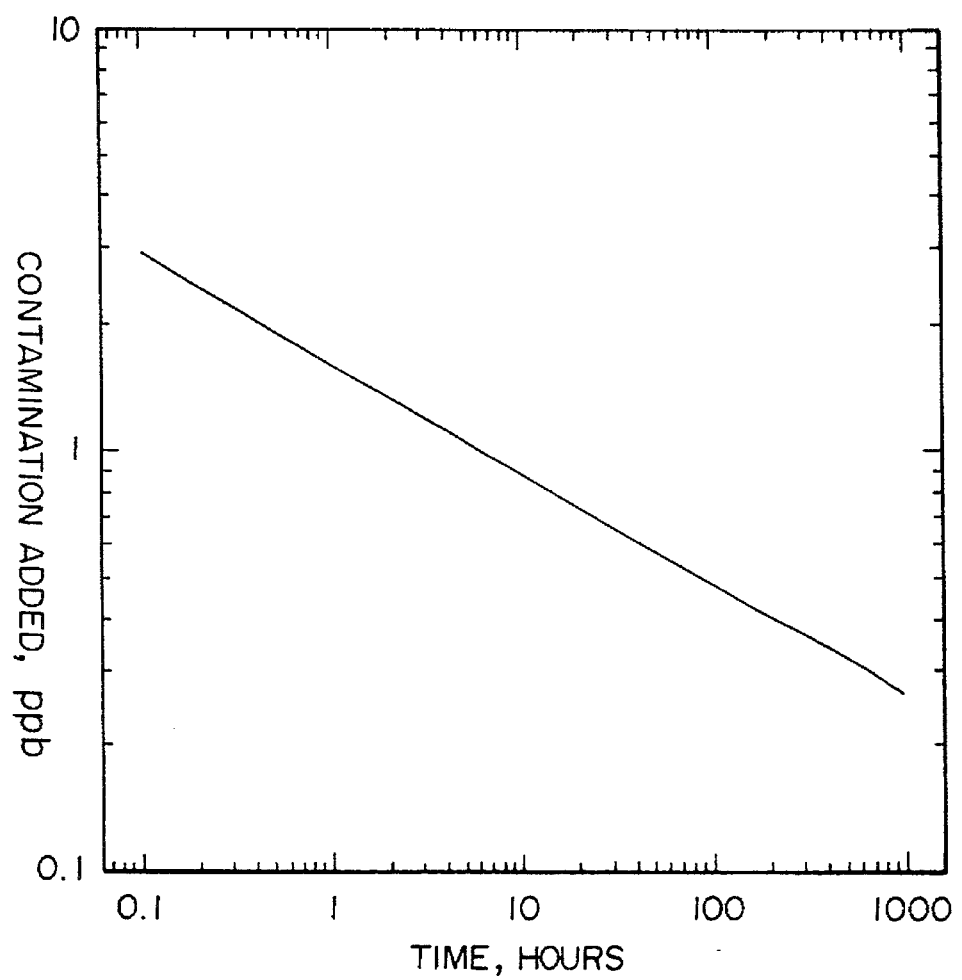
FIG. 5 is a graph of contaminant concentration increases in a chemical delivery system delivering a known volume of chemical, obtained from the graph in FIG. 4.
Figure 6:
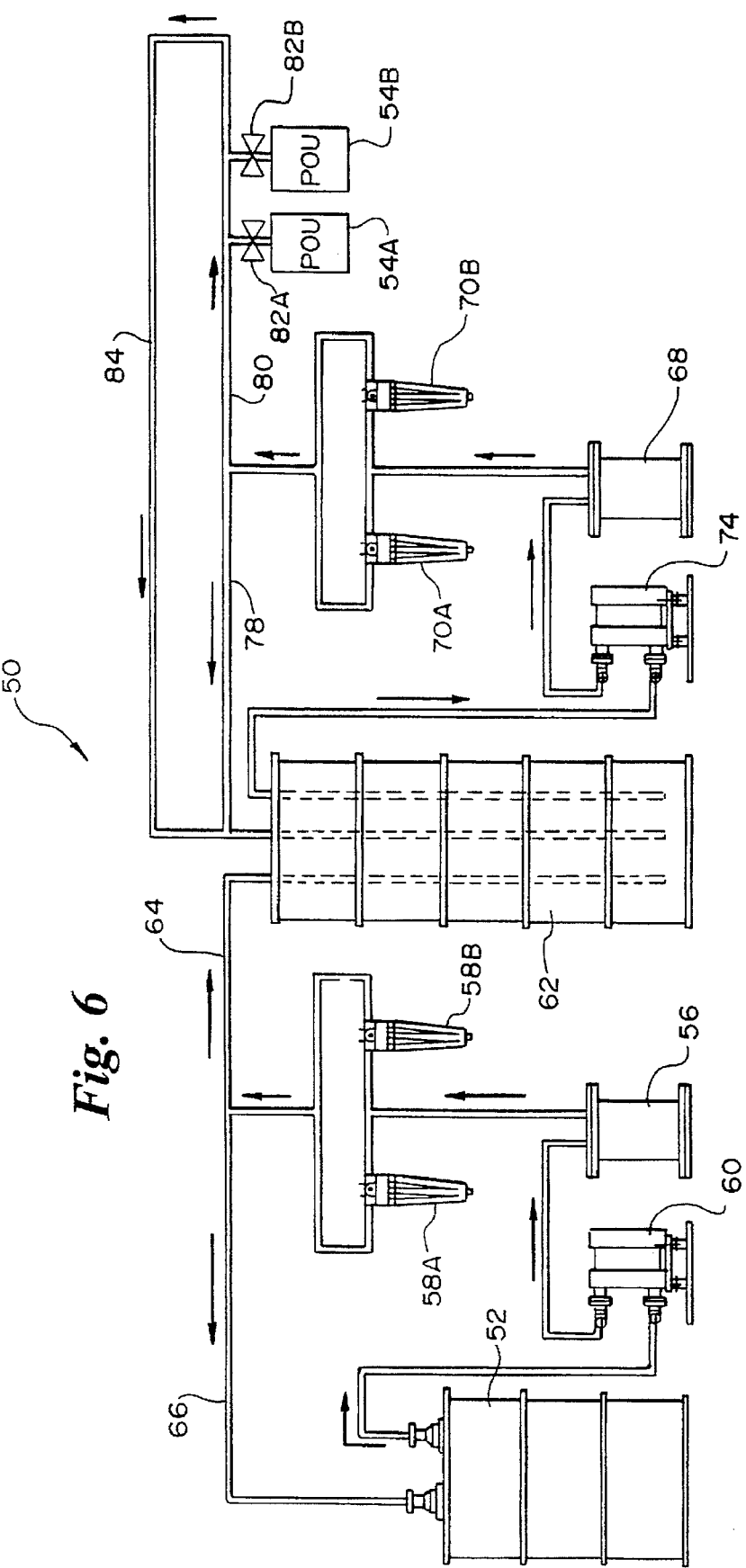
FIG. 6 is a block and diagrammatic illustration of a chemical distribution system used to perform and test the dynamic contaminant extraction measurement method of the present invention, and which can be qualified by the method.

FIG. 5 is a graph of Equation 3 and shows the concentration of contamination added over time. FIG. 5 can be used to visualize the time when the system meets specification.

During the above-described test of system 10, several chemical samples were identified as having been inadvertently contaminated on the basis of the contaminant measurements. The following description is representative of the manner by which these contaminated samples were identified. The background calcium contamination measurement was 0.2 ppb. The measured calcium concentration in the sample taken at 0.1 hours was 2.1 ppb. However, the measured calcium concentration in subsequent samples ranged between 0.1 ppb and 0.3 ppb. Since it is highly unlikely that the concentration of calcium or any other contaminant would increase and subsequently decrease in the same volume of chemical, the calcium concentration measurement from the 0.1 hour sample was discarded. Alternatively, the value could have been replaced with an average of adjacent calcium concentration measurements.

The dynamic contaminant extraction measurement method of the present invention can also be used to qualify chemical distribution systems (i.e., to determine when the amount of extraction from a newly assembled or installed system has decreased to an acceptable specification or operating level). A test of the dynamic extraction method for this purpose was conducted on a chemical distribution system 50 shown in FIG. 5. Chemical distribution system 50 is used to distribute bulk chemicals from supply drum 52 to one or more points-of-use 54A and 54B in a semiconductor fabrication facility. Chemical distribution systems of this type are generally known, and commercially available from a number of sources including FSI International of Chaska, Minn., the assignee of the present invention.

Chemical from supply drum 52 is pumped through a pulse-dampening receiver 56 and filters 58A and 58B by pump 60. The chemical is polished by recirculating the chemical back to the supply drum 52 through line 66 for a predetermined time period, and is then transferred to day tank 62 through line 64. From day tank 62 the chemical is pumped through pulse-dampening receiver 68 and filters 70A and 70B by pump 74. System 50 can be operated with either internal or external stabilized flow. With internal stabilized flow, a portion of the filtered chemical is returned to day-tank 62 through recirculation flow line 78, while a distribution flow portion of the filtered chemical is supplied to points-of-use 54A and 54B through flow Line 80 and valves 82A and 82B, respectively. With external stabilization, there is no flow through line 78. Instead, portions of the distribution flow of chemical that are not used at the points-of-use 54A and 54B are returned to day tank 62 through recirculation flow line 84 as a full fab recirculation stabilization flow.

For purposes of the test, day tank 62 was filled with a known quantity of 49% HF. Valves 82A and 82B remained closed (except to remove samples), and pump 74 was actuated to continuously circulate the chemical from the day tank through receiver 68, filters 70A and 70B, and back to the day tank through flow lines 78 and 84. A background sample of the chemical was taken before filling day tank 62. Samples of the circulating chemical were also taken after twenty-three, forty-seven, ninety-five and one hundred and ninety-one hours of continuous operation of system 50. The samples were handled and measured for concentration of extracted contaminants in a manner similar to the procedure used in connection with test system 10 described above. Table 1 below lists the measured concentrations of potassium, sodium and nickel, and the total metallics concentration, for each of the samples. The background concentrations are listed under the sample time of zero.

TABLE 1

| Time, hours | Total Metallics, ppb | Potassium, ppb | Sodium, ppb | Nickel, ppb |
| --- | --- | --- | --- | --- |
| 0 | 14.5 | <0.30 | 0.85 | <0.1 |
| 23 | 45.3 | 30.1 | 2.21 | <0.1 |
| 47 | 14.2 | <0.30 | 0.81 | <0.1 |
| 95 | 42.6 | 21.0 | 0.89 | 1.4 |
| 191 | 15.0 | 0.34 | 0.92 | <0.1 |

Since it is unlikely that the concentration of individual contaminants would increase and subsequently decrease by large amounts over adjacent samples, the potassium measurements at twenty-three and ninety five hours, the sodium measurements at twenty-three hours and the nickel measurement at ninety-five hours are almost certainly in error. Accordingly, averages of the adjacent concentration measurements were substituted for erroneous measurements above the detection limit, and concentrations at the detection limit were substituted for concentrations below the detection limit. Table 2 below lists the "corrected" concentration data.

TABLE 2

| Time, hours | Total Metallics, ppb | Potassium, ppb | Sodium, ppb | Nickel, ppb |
| --- | --- | --- | --- | --- |
| 0 | 14.5 | <0.30 | 0.85 | <0.1 |
| 23 | 14.2 | <0.30 | 0.83 | <0.1 |
| 47 | 14.2 | <0.30 | 0.81 | <0.1 |
| 95 | 20.6 | 0.32 | 0.89 | <0.1 |
| 191 | 15.0 | 0.34 | 0.92 | <0.1 |

When this data is plotted and/or a regression is performed, Equation 4 below is found to characterize the contaminant concentration as a function of time.

$$C_r = 14.1 t^{0.029} \qquad \text{Eq. 4}$$

Where:

t=time in hours; and $C_r$=Concentration in ppb.

The mass of contaminants in system 50 can be determined by multiplying Equation 4 by the volume of chemical in the system (400 liters) to obtain Equation 5.

$$M_r = 5640 t^{0.029} \qquad \text{Eq. 5}$$

Where:

$M_r$=mass in micrograms; and t=time.

Taking the derivative of Equation 5, the extraction rate is given by Equation 6 below.

$$R_r = 163 t^{-0.971} \qquad \text{Eq. 6}$$

Where:

t=time in hours; and $R_r$=extraction rate in micrograms/hour.

The concentration increase resulting from the extracting mass can be calculated by dividing Equation 6 by the chemical usage. For a system 50 delivering 200 liters/day (8.31/hr) the contamination added is given by Equation 7 below.

$$C_A = 19.6 t^{-0.971} \qquad \text{Eq. 7}$$

Where:

$C_A$=contaminant added in ppb; and
t=time in hours.

From Equation 7, the contaminant concentration added to system 50 at the twenty-three and one hundred and ninety-one hour sample times is found to be the values listed below in Table 3.

TABLE 3

| Time, hours | Contaminant Addition Rate, ppb |
|---|---|
| 23 | 0.94 |
| 191 | 0.098 |

On the basis of the corrected measurement data, system 50 is characterized as adding about 0.9 ppb of total contaminants to the chemical after twenty-three hours of circulation, rather than the 30.8 ppb that would have been indicated by the measurement data had the erroneous samples not been identified and corrected. Contaminant concentration added is shown as reducing to about 0.10 ppb after one hundred and ninety-one hours of circulation.

Chemical distribution systems such as 50 will typically be characterized by a specification describing an acceptable level of added contaminants. Using the extraction rate determined in the manner described above, it is possible to accurately predict the length of time that the chemical should be circulated in the system to reduce the amount of added contaminants to the specification value. The chemical can then be recirculated through the system for the calculated time period, and the system qualified thereafter without even having to analyze another sample. The chemical circulated through the chemical distribution system during the qualification procedure can then be discarded, and the system operated in a conventional manner.

The dynamic contaminant extraction measurement method described above offers considerable advantages over prior art techniques. The amount of chemical required for qualification is reduced since the same volume of chemical is used throughout the test. The test procedure can be performed relatively quickly since there is no down time unused by as fresh batches of chemical being loaded into and flushed from the system. The ability to predict the future performance of the system is also important. All these characteristics increase the efficiency of the qualification process. The method also offers improved accuracy since contaminated sample measurement errors can be identified and corrected. Measurement sensitivity is increased (smaller amounts of added contaminants can be measured) since the same volume of chemical is used throughout the procedure. Surface contamination and bulk extraction can be separately identified.

Although the present invention has been described with reference to preferred embodiments, those skilled in the art will recognize that changes can be made in form and detail without departing from the spirit and scope of =the invention.

What is claimed is:

1. A method for dynamically measuring the extraction of surface and bulk contaminants from a component upon exposure to a liquid chemical to determine if the contaminant extraction rate is sufficiently low to qualify the component for use in a high purity system, including:

continuously circulating a volume of the liquid chemical past the component, thereby subjecting said component to liquid chemical exposure periodically measuring the concentration of contaminants in the volume of liquid chemical;

determining the rate of extraction of contaminants from as a function of the concentration measurements; and qualifying the component for use in the high purity system as a function of the contaminant extraction rate determined from the concentration measurements made on the volume of liquid chemical.

2. The method of claim 1 wherein:

circulating a volume of liquid chemical includes continuously circulating a known volume of the liquid chemical past the component; and measuring the concentration of contaminants includes determining the individual type or total mass of contaminants in the liquid chemical.

3. The method of claim 1 wherein measuring the concentration of contaminants includes:

removing representative liquid samples from the circulating liquid chemical; and measuring the concentration of contaminations in the representative liquid samples.

4. The method of claim 1 wherein measuring the concentration of contaminants includes measuring the concentration of contaminants about one tenth of an hour plus or minus one twentieth of an hour after the initiation of chemical circulation past the component to determine surface contamination of the component.

5. The method of claim 1 wherein periodically measuring the quantity of contaminants includes measuring the quantity of contaminants about an hour plus or minus one half an hour after the initiation of chemical circulation past the component.

6. The method of claim 1 wherein periodically measuring the quantity of contaminants includes measuring the quantity of contaminants about ten hours plus or minus one hour after the initiation of chemical circulation past the component.

7. Qualifying a chemical distribution system on the basis of the contaminant measurements made in accordance with the method of claim 1.

8. A method for dynamically measuring the extraction of surface and bulk contaminants from one or more components upon exposure to a liquid chemical to determine if the contaminant extraction rate is sufficiently low to qualify the component for use in a high purity system, including:

providing a supply tank containing a volume of the liquid chemical;

providing a fluid flow circulation line having an inlet and an outlet in fluid communication with the tank, with the components positioned in fluid communication with the circulation line;

continuously circulating the volume of liquid chemical though the circulation line past the past the components, thereby subjecting said components to liquid chemical exposure periodically measuring the concentration of contaminants in the volume of chemical; determining the rate of extraction of contaminants from the components as a function of the concentration measurements; and qualifying the components for use as a function of the contaminant extraction rate determined from the concentration measurements made on the volume of liquid chemical.

9. The method of claim 8 wherein:

providing the tank of chemical includes providing a tank containing a known volume of the chemical; and periodically measuring the concentration of contaminants includes determining the mass of extracted contaminants in the chemical.

10. The method of claim 8, wherein measuring the concentration of contaminants includes measuring the concentration of contaminants about one tenth of an hour plus or minus one twentieth of an hour after the initiation of chemical circulation past the component to determine surface contamination of the component.

11. Qualifying a chemical distribution system using the method of claim 8.

12. A method for qualifying a chemical distribution system with circulating fluid that has a chemical supply tank and a recirculation flow line with associated fluid handling and fluid transfer components thru which liquid chemical can be circulated, so as to achieve a predetermined specification level of surface and bulk purity of the system, including:

filling the tank with chemical;

continuously circulating the chemical through the recirculation flow line;

periodically measuring the concentrations of extracted contaminants in the circulating chemical;

determining the contaminant extraction rate as a function of the measured concentrations; and qualifying the system for production when the extraction rate has decreased to a predetermined specification level; and discontinuing the chemical circulation after the predetermined specification level of the chemical distribution system is achieved.

* * * * *

UNITED STATES PATENT AND TRADEMARK OFFICE
CERTIFICATE OF CORRECTION

PATENT NO. : 5,641,895
DATED : June 24, 1997
INVENTOR(S) : Donald C. Grant

It is certified that error appears in the above-indentified patent and that said Letters Patent is hereby corrected as shown below:

Column 7, line 65, insert --;-- at the end of the line

Column 8, line 1, insert --the component-- after "from"

Column 8, line 18, delete "contaminations" and insert therefor --contaminants--

Column 8, line 42, delete "component" and insert therefor --components--

Column 8, line 50, delete the second occurrence of the phrase "past the"

Column 8, line 52, insert --;-- at the end of the line

Signed and Sealed this

Twenty-first Day of October 1997

*Attest:*

BRUCE LEHMAN

*Attesting Officer*     *Commissioner of Patents and Trademarks*